US011413345B2

United States Patent
Li et al.

(10) Patent No.: US 11,413,345 B2
(45) Date of Patent: Aug. 16, 2022

(54) SYNTHETIC HEMAGGLUTININ AS UNIVERSAL VACCINE AGAINST INFECTION BY TYPE B INFLUENZA VIRUSES (IBV)

(71) Applicant: Her Majesty the Queen in the Right of Canada as Represented by the Minister of Health, Winnipeg (CA)

(72) Inventors: Xuguang Li, Winnipeg (CA); Gary Van Domselaar, Winnipeg (CA); Adrian Zetner, Winnipeg (CA)

(73) Assignee: Her Majestry the Queen in Right of Canada as Represented by the Minister of Health, Winnipeg (CA)

( * ) Notice: Subject to any disclaimer, the term of this patent is extended or adjusted under 35 U.S.C. 154(b) by 0 days.

(21) Appl. No.: 16/648,439

(22) PCT Filed: Nov. 16, 2018

(86) PCT No.: PCT/CA2018/051455
§ 371 (c)(1),
(2) Date: Mar. 18, 2020

(87) PCT Pub. No.: WO2019/100147
PCT Pub. Date: May 31, 2019

(65) Prior Publication Data
US 2020/0306363 A1 Oct. 1, 2020

Related U.S. Application Data

(60) Provisional application No. 62/589,908, filed on Nov. 22, 2017.

(51) Int. Cl.
*A61K 39/145* (2006.01)
*A61K 9/00* (2006.01)
*A61K 39/00* (2006.01)
*C12N 7/00* (2006.01)

(52) U.S. Cl.
CPC .......... *A61K 39/145* (2013.01); *A61K 9/0043* (2013.01); *C12N 7/00* (2013.01); *A61K 2039/5258* (2013.01); *A61K 2039/543* (2013.01); *C12N 2760/16234* (2013.01)

(58) Field of Classification Search
CPC ........... C12N 2760/16034; C12N 2760/16223; C12N 2760/16162; C12N 2760/18021; C12N 2710/10343; C12N 2710/20034; C12N 2740/11034; C12N 2740/16034; C12N 2710/20023; C12N 2710/20071; C12N 2730/10122; C12N 2730/10123; C12N 2730/10134; C12N 2730/10171; C12N 2740/14034; C12N 2740/15023; C12N 2740/15051; C12N 2740/16023; C12N 2760/00034; C12N 2760/14123; C12N 2760/16023; A61K 39/145; A61K 2039/5258
See application file for complete search history.

(56) References Cited

U.S. PATENT DOCUMENTS

| | | | |
|---|---|---|---|
| 9,452,211 B2 * | 9/2016 | Meijberg | A61K 39/145 |
| 2014/0357845 A1 * | 12/2014 | Meijberg | C12N 7/00 530/396 |
| 2016/0355553 A1 | 12/2016 | Meijberg et al. | |
| 2016/0362455 A1 | 12/2016 | Meijberg et al. | |

FOREIGN PATENT DOCUMENTS

| | | | | |
|---|---|---|---|---|
| WO | 2010117786 | | 10/2010 | |
| WO | 2013079473 | | 6/2013 | |
| WO | WO2013/0794473 A1 * | | 6/2013 | A61K 39/12 |

OTHER PUBLICATIONS

A. Duran, Master Thesis "Investigation of a Trimeric Hemagglutinin Stem Domain form Influenza B for a Universal Vaccine", Sep. 28, 2018, pp. 1-108.

* cited by examiner

Primary Examiner — Bao Q Li
(74) Attorney, Agent, or Firm — Michael R Williams; Ryan W Dupuis; Ade & Company Inc.

(57) ABSTRACT

A synthetic hemagglutinin (sHA) which represents the highest degree of conservation in the HA sequences of all Influenza B viruses (IVB) based on comprehensive bioinformatics analyses was cloned into an adenoviral vector. The recombinant adenovirus carrying the sHA gene was then delivered intransallyintranasally into DAB/2 mice. The animals were challenged with 5xLD50 influenza B viruses. We have found that the synthetic HA vaccines afford 100% protection against lethal challenge whereas 50% mice died in the control group. Furthermore, no virus was found in the lung of the vaccinated group while significant lung viruses were found in all mice of the controlled group. Consistent with the survival data and virus titre, severe pneumonia was found in all mice of the control group while no pathologic observation was made in animals receiving the vaccines.

23 Claims, 7 Drawing Sheets

Specification includes a Sequence Listing.

SEQUENCE LISTING

<160> NUMBER OF SEQ ID NOS: 5

<210> SEQ ID NO 1
<211> LENGTH: 223
<212> TYPE: PRT
<213> ORGANISM: Influenza B virus

<400> SEQUENCE: 1

```
Gly Phe Phe Gly Ala Ile Ala Gly Phe Leu Glu Gly Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Glu Ile Gly Asn Gly Cys Phe Glu Thr Lys His Lys Cys
    130                 135                 140

Asn Gln Thr Cys Leu Asp Arg Ile Ala Ala Gly Thr Phe Asn Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190
```

```
Thr Ala Ala Ser Ser Leu Ala Val Thr Leu Met Leu Ala Ile Phe Ile
        195                 200                 205

Val Tyr Met Val Ser Arg Asp Asn Val Ser Cys Ser Ile Cys Leu
    210                 215                 220

<210> SEQ ID NO 2
<211> LENGTH: 223
<212> TYPE: PRT
<213> ORGANISM: Influenza B virus
<220> FEATURE:
<221> NAME/KEY: VARIANT
<222> LOCATION: (132)..(132)
<223> OTHER INFORMATION: D or E
<220> FEATURE:
<221> NAME/KEY: VARIANT
<222> LOCATION: (158)..(158)
<223> OTHER INFORMATION: N or D
<220> FEATURE:
<221> NAME/KEY: VARIANT
<222> LOCATION: (204)..(204)
<223> OTHER INFORMATION: I or L
<220> FEATURE:
<221> NAME/KEY: VARIANT
<222> LOCATION: (208)..(208)
<223> OTHER INFORMATION: I or V
<220> FEATURE:
<221> NAME/KEY: VARIANT
<222> LOCATION: (212)..(212)
<223> OTHER INFORMATION: V or I

<400> SEQUENCE: 2

Gly Phe Phe Gly Ala Ile Ala Gly Phe Leu Glu Gly Trp Glu Gly
1               5                   10                  15

Met Ile Ala Gly Trp His Gly Tyr Thr Ser His Gly Ala His Gly Val
            20                  25                  30

Ala Val Ala Ala Asp Leu Lys Ser Thr Gln Glu Ala Ile Asn Lys Ile
        35                  40                  45

Thr Lys Asn Leu Asn Ser Leu Ser Glu Leu Glu Val Lys Asn Leu Gln
    50                  55                  60

Arg Leu Ser Gly Ala Met Asp Glu Leu His Asn Glu Ile Leu Glu Leu
65                  70                  75                  80

Asp Glu Lys Val Asp Asp Leu Arg Ala Asp Thr Ile Ser Ser Gln Ile
                85                  90                  95

Glu Leu Ala Val Leu Leu Ser Asn Glu Gly Ile Ile Asn Ser Glu Asp
            100                 105                 110

Glu His Leu Leu Ala Leu Glu Arg Lys Leu Lys Lys Met Leu Gly Pro
        115                 120                 125

Ser Ala Val Xaa Ile Gly Asn Gly Cys Phe Glu Thr Lys His Lys Cys
    130                 135                 140

Asn Gln Thr Cys Leu Asp Arg Ile Ala Ala Gly Thr Phe Xaa Ala Gly
145                 150                 155                 160

Glu Phe Ser Leu Pro Thr Phe Asp Ser Leu Asn Ile Thr Ala Ala Ser
                165                 170                 175

Leu Asn Asp Asp Gly Leu Asp Asn His Thr Ile Leu Leu Tyr Tyr Ser
            180                 185                 190

Thr Ala Ala Ser Ser Leu Ala Val Thr Leu Met Xaa Ala Ile Phe Xaa
        195                 200                 205

Val Tyr Met Xaa Ser Arg Asp Asn Val Ser Cys Ser Ile Cys Leu
    210                 215                 220

<210> SEQ ID NO 3
<211> LENGTH: 669
```

```
<212> TYPE: DNA
<213> ORGANISM: Influenza B virus

<400> SEQUENCE: 3
gggtttttcg gcgccatcgc cggcttcctg gagggcggct gggagggcat gatcgccggc    60
tggcacggct acaccagcca cggcgcccac ggcgtggccg tggccgccga cctgaagagc   120
acccaggagg ccattaacaa gatcacaaag aacctgaaca gcctgtccga gctggaggtg   180
aagaacctgc agaggctgag tggcgccatg gatgagctgc acaacgagat cctggagctg   240
gacgagaagg tggatgacct gagggctgac accatcagct ctcagattga gctggccgtg   300
ctgctgtcta acgagggcat catcaacagc gaggacgagc acctgctggc cctggagaga   360
aagctgaaga agatgctggg accctccgcc gtggagatcg gaaacggctg ctttgagacc   420
aagcacaagt gcaaccagac ctgtctggac agaatcgccg ccggcacctt caatgccgga   480
gagttcagcc tgcccacctt cgacagcctg aacatcaccg ccgctagcct gaacgacgac   540
ggactggaca ccacaccat cctgctgtac tacagcacag ccgccagctc cctggccgtc   600
accctgatgc tggccatctt catcgtgtac atggtgagca gagataacgt gtcttgttcc   660
atctgcctg                                                          669

<210> SEQ ID NO 4
<211> LENGTH: 23
<212> TYPE: PRT
<213> ORGANISM: artificial sequence
<220> FEATURE:
<223> OTHER INFORMATION: Signal sequence peptide

<400> SEQUENCE: 4

Met Leu Leu Ala Val Leu Tyr Cys Leu Leu Trp Ser Phe Gln Thr Ser
1               5                  10                  15

Ala Gly His Phe Pro Arg Ala
            20

<210> SEQ ID NO 5
<211> LENGTH: 27
<212> TYPE: PRT
<213> ORGANISM: artificial sequence
<220> FEATURE:
<223> OTHER INFORMATION: trimerization motif peptide

<400> SEQUENCE: 5

Tyr Ile Pro Glu Ala Pro Arg Asp Gly Gln Ala Tyr Val Arg Lys Asp
1               5                  10                  15

Gly Glu Trp Val Leu Leu Ser Thr Phe Leu Gly
            20                  25
```

SYNTHETIC HEMAGGLUTININ AS UNIVERSAL VACCINE AGAINST INFECTION BY TYPE B INFLUENZA VIRUSES (IBV)

PRIOR APPLICATION INFORMATION

The instant application is a 371 of Patent Co-operation Treaty Application PCT CA2018/051455, filed Nov. 16, 2018, now abandoned, which claimed the benefit of US Provisional Patent Application U.S. Ser. No. 62/589,908, filed Nov. 22, 2018 and entitled "SYNTHETIC HEMAGGLUTININ AS UNIVERSAL VACCINE AGAINST INFECTION BY TYPE B INFLUENZA VIRUSES (IBV)", the contents of which are incorporated herein by reference.

BACKGROUND OF THE INVENTION

Influenza can infect as much as 5-15% of the world population, resulting in 3-5 million cases of severe illness and up to 500,000 deaths per year. In the US alone, flu epidemics lead to approximately 300,000 influenza-related hospital admissions and 36,000 influenza related deaths annually in addition to an estimated cost of $12 billion per year. Current seasonal influenza vaccines are produced with strains recommended by the World Health Organization about 9-12 months ahead of the targeted season. The vaccines typically contain two type A influenza strains and one type B influenza strain, which are predicted to be the most likely strains to cause the upcoming flu epidemic.

However, there are inherent disadvantages associated with the preparation of conventional influenza vaccines such as the uncertainty of the actual circulating strain, the need for annual updating of the manufacturing process and preparation of reagents for vaccine lot release. Clearly, the drawbacks associated with traditional vaccine preparation would be drastically exacerbated in the event of an outbreak of pandemic influenza, given a perceivably much shortened timeframe available for the production of prophylactic vaccines for global needs. All these problems concerning the influenza vaccines are largely due to one single biological property of the influenza virus itself, i.e. the constant mutations of the virus surface proteins hemagglutinin (HA) and neuraminidase (NA).

The make-up of the main influenza antigen, hemagglutinin (HA), changes constantly in circulating strains of both influenza type A virus and influenza type B virus (IBV). IBV is responsible for up to a quarter of annual influenza infections, on an annual basis.

There remains a need in the art for therapies and prevention strategies that can be used to prevent a wide range of infection by various influenza strains.

SUMMARY OF THE INVENTION

According to an aspect of the invention, a method of immunizing an individual in need of such treatment against Influenza virus B comprising administering to said individual an effective amount of the protein as set forth in SEQ ID No:1 or SEQ ID No:2.

According to another aspect of the invention, there is provided an IBV stem protein comprising the amino acid sequence as set forth in SEQ ID No: 1 or SEQ ID No:2.

According to a further aspect of the invention, there is provided a nucleic acid as set forth in SEQ ID No:3 or the nucleic acid deduced from the amino acid sequence of SEQ ID No:1 or the nucleic acid deduced from the amino acid sequence of SEQ ID No:2 operably linked to a suitable promoter.

According to a still further aspect of the invention, there is provided an expression system comprising the nucleic acid as set forth in SEQ ID No:3 or the nucleic acid deduced from the amino acid sequence of SEQ ID No:1 or the nucleic acid deduced from the amino acid sequence of SEQ ID No:2 operably linked to a suitable promoter.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The practice of the present invention will employ, unless otherwise indicated, conventional methods of chemistry, biochemistry, recombinant DNA techniques and immunology, within the skill of the art. Such techniques are explained fully in the literature. See, e.g., Fundamental Virology, 2nd Edition, vol. I & II (B. N. Fields and D. M. Knipe, eds.); Handbook of Experimental Immunology, Vols. I-IV (D. M. Weir and C. C. Blackwell eds., Blackwell Scientific Publications); T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.).

It must be noted that, as used in this specification and the appended claims, the singular forms "a", "an" and "the" include plural referents unless the content clearly dictates otherwise. Thus, for example, reference to "an antigen" includes a mixture of two or more antigens, and the like.

The following amino acid abbreviations are used throughout the text:

Alanine: Ala (A) Arginine: Arg (R) Asparagine: Asn (N) Aspartic acid: Asp (D) Cysteine: Cys (C) Glutamine: Gln (Q) Glutamic acid: Glu (E) Glycine: Gly (G) Histidine: His (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V)

Definitions:

In describing the present invention, the following terms will be employed, and are intended to be defined as indicated below.

The terms "polypeptide" and "protein" refer to a polymer of amino acid residues. Thus, peptides, oligopeptides, dimers, multimers, and the like, are included within the definition.

By "antigen" is meant a molecule, which contains one or more epitopes that will stimulate a host's immune system to make a cellular antigen-specific immune response when the antigen is presented, or a humoral antibody response.

An "immunological response" to a selected antigen or composition is the development in a subject of a humoral and/or a cellular immune response to epitopes or molecules present in the composition of interest. For purposes of the present invention, a "humoral immune response" refers to an immune response mediated by antibody molecules, while a "cellular immune response" is one mediated by T-lymphocytes and/or other white blood cells.

The terms "effective amount" or "pharmaceutically effective amount" of an adjuvant composition and antigen, as provided herein, refer to a nontoxic but sufficient amount of the composition to provide the desired response, such as an immunological response. As will be pointed out below, the exact amount required will vary from subject to subject, depending on the species, age, and general condition of the subject, mode of administration, and the like. An appropriate "effective" amount in any individual case may be determined by one of ordinary skill in the art using routine experimentation.

Described herein is an antigenic protein derived from a trimeric influenza hemagglutinin (HA) stem domain from influenza B virus and the use thereof as a vaccine.

Specifically, there is provided a synthetic hemagglutinin (sHA) which represents the highest degree of conservation in the HA sequences of all IBV based on comprehensive bioinformatics analyses as discussed herein.

The Hemagglutinin (HA) protein has two subunits: HA1, which is the head of the protein and HA2, which is the stem of the HA protein. HA1 is constantly mutating because of the immune pressure from viral hosts, such as for example animals and birds. The HA2 subunit on the other hand is shielded by HA1 and consequently is subjected to less immune pressure by viral hosts. As such, it is highly conserved. It is of note that immediately outside of this approximately 230 amino acid domain is the highly variable HA1 subunit.

Figure 3:
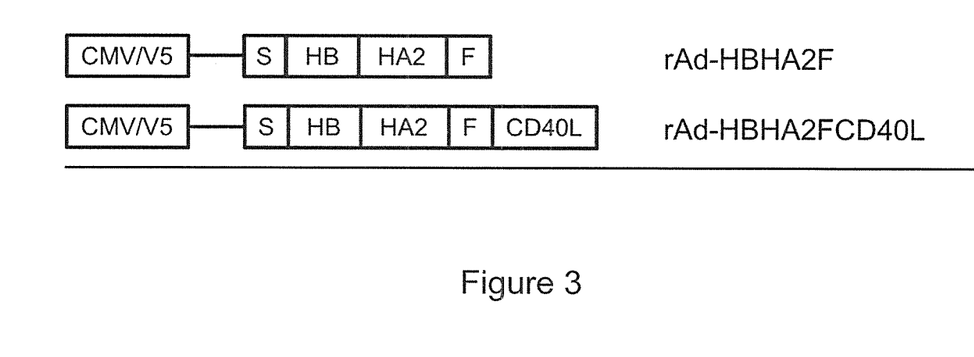
FIG. 3 shows the structure of the two vaccine constructs: rAd-HBHA2F and rAd-HBHA2FCD40L. These genes were cloned into rAd vector under the control of CMV promoter. "S" denotes secretion signal, "HB" denotes the HA2 of IBV HA, "F" denotes "trimerizing motif".
Figure 4A:
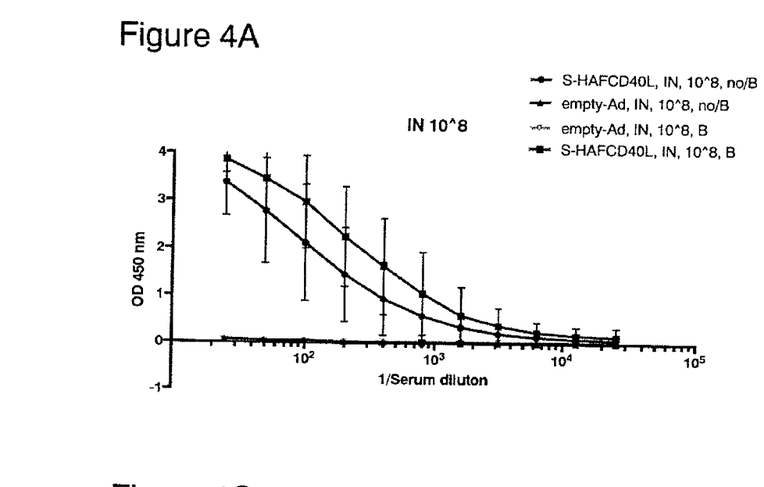
FIG. 4 shows antibody titer analysis. Panels A and B show after intra-nasal administration of the vaccine with CD40 ligand, the antibodies titres are higher than the vector controls. Panels C & D shows the same except the administration route is sub-cutaneous.
Figure 4B:
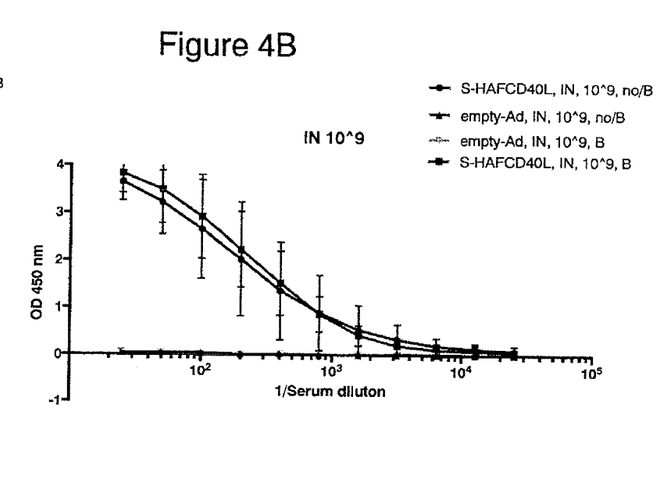
Figure 4C:
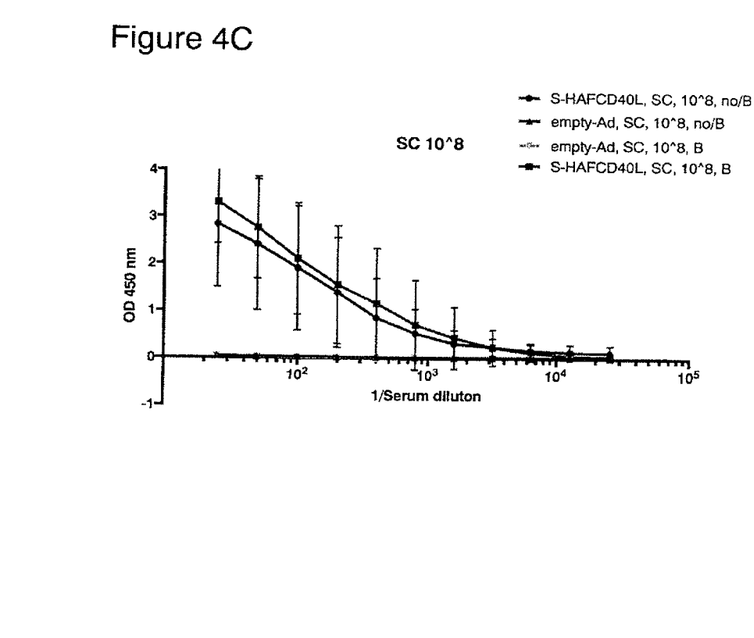
Figure 4D:
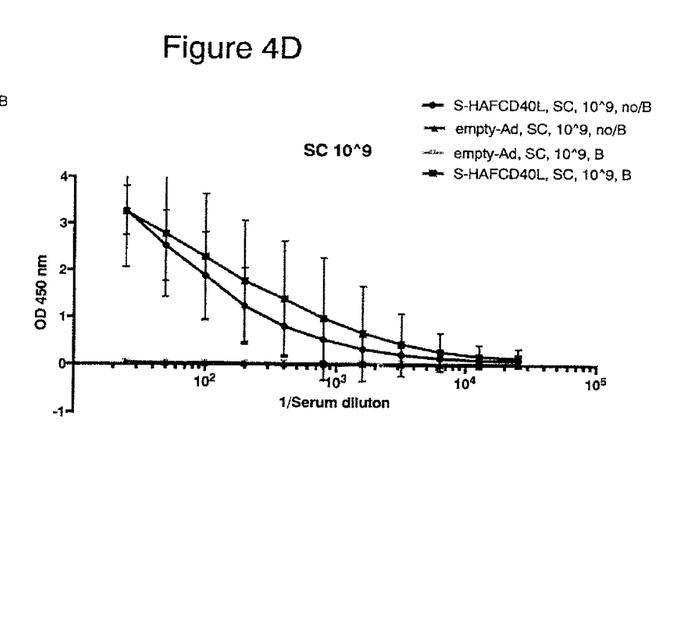

As discussed herein, two vaccine constructs were prepared: rAd-HBHA2F which is the synthetic hemagglutinin protein (HA2 subunit of HA) without CD40 ligand and rAd-HBHA2FCD40L which includes with CD40 ligand, shown in FIG. 3. These genes were cloned into rAd vector under the control of CMV promoter. "S" denotes secretion signal, "HB" denotes the HA2 of IBV HA, "F" denotes "trimerizing motif".

The recombinant adenovirus carrying the sHA gene was then delivered intranasally into DAB/2 mice. 28 days later, the animals were boosted with another dose of the recombinant adenovirus vaccine. On day 56, the animals were challenged with 5xLD50 influenza B viruses. We then observed the animals for two more weeks (survival studies). The survival rates were obtained (FIG. 5), along with sera for antibody analyses (FIG. 4), tissues for pathological analyses (FIG. 6) (lung viral titre) and spleen cells for cytokine quantification (Table 1). We have found that the synthetic HA vaccines afforded 100% protection against lethal challenge irrespective of the presence of CD4 ligand whereas 50% of the mice in the control group died. Furthermore, no virus was found in lung tissue samples of the vaccinated group while significant levels of viruses were found in the lung tissue samples of all mice of the control group. Consistent with the survival data and virus titre, severe pneumonia was found in all mice of the control group while no pathologic damage was observed in animals receiving the vaccines, as discussed herein.

As discussed herein, the antigenic peptide may be used for immunization of an individual against influenza B. Specifically, the peptide is shown to protect animals, for example, a mammal such as a human, from influenza B virus challenge.

Figure 1:
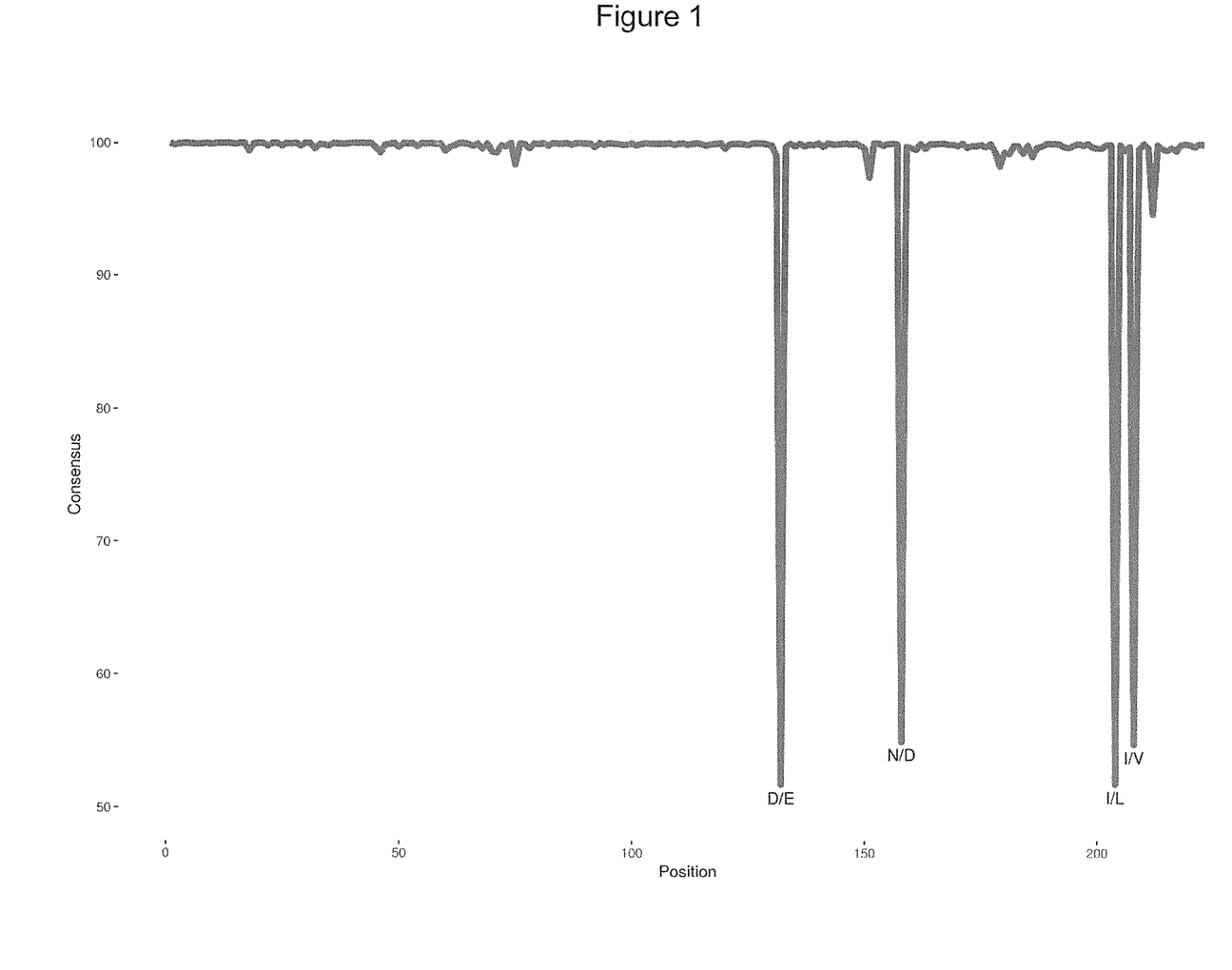
FIG. 1 is a schematic diagram of the main sequence variants in Influenza Virus B stem subunit.
Figure 2:
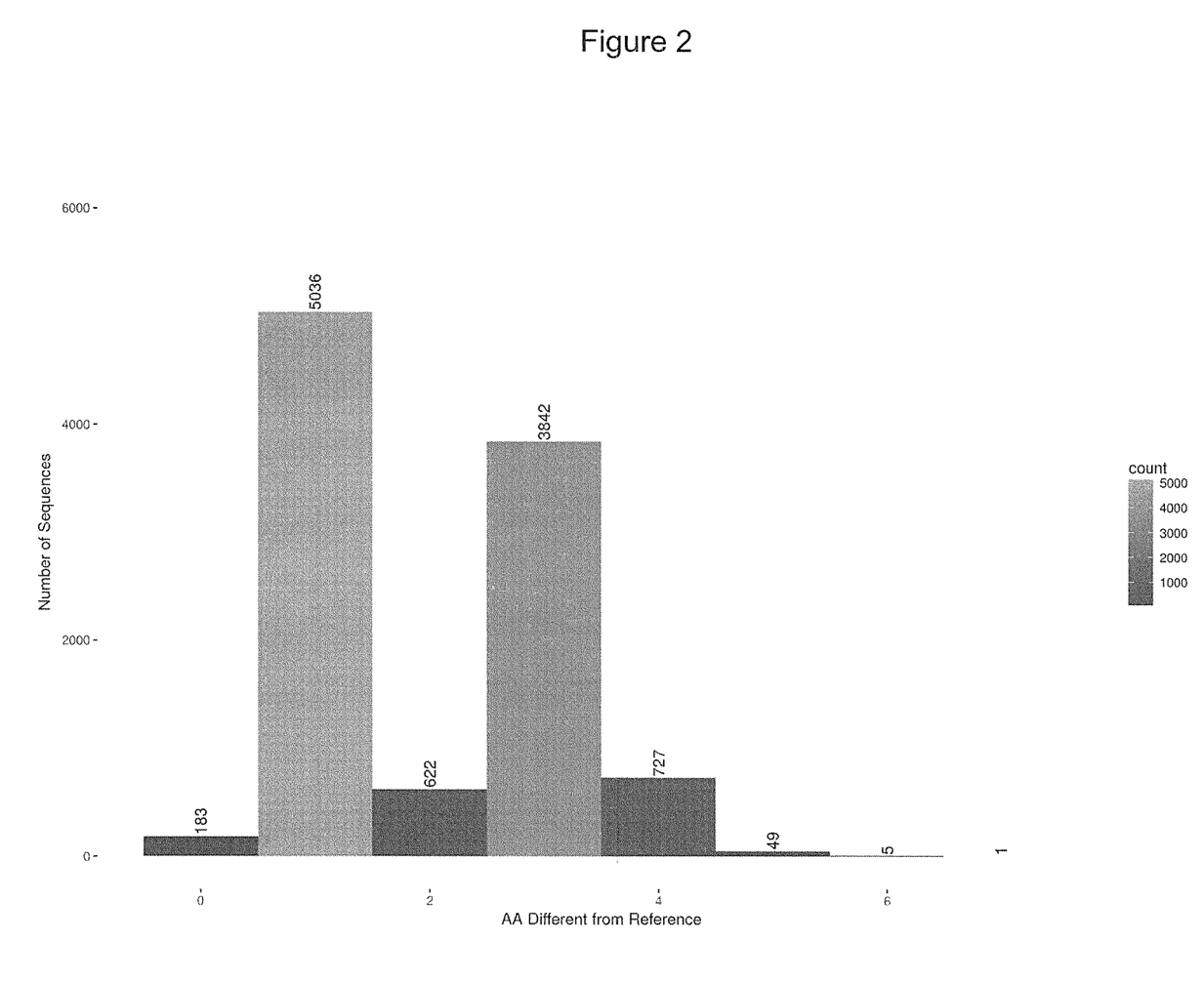
FIG. 2 is a bar graph showing the number of strains of Influenza Virus B having 0-7 amino acids different from the sHA stem protein.

In some embodiments, the protein is a synthetic polypeptide which is essentially the HA2 (stem) domain of the HA protein of IBV. Specifically, the synthetic protein is approximately 230 amino acids in length and is based on a consensus sequence of the HA2 stem domain, which was developed based on computational analysis of approximately 8,000 different strains of IBV. All publicly available InfB HA2 sequences were downloaded from NCBI as of March 2016. The sequences were multiply aligned, and each position scanned for variation. The variant with the highest representation in each position was chosen for the consensus. The stem region is highly conserved, having greater than 95% identity across the different strains of IBV, for all but five positions (see FIG. 1). Note that there are 183 known sequences that are identical to the consensus sequence (FIG. 2).

As will be appreciated by one of skill in the art, the (VB stem domain protein is not a 'peptide' in the sense that peptides are typically 10-50 AA. For example, as will be well known to those of skill in the art, peptides up to around 10 aa are unstructured while peptides between 10 and 50 aa can form stable secondary structures like helices and sheets, and can fold on each other. Peptides are usually conjugated to carrier proteins to help solubilize and increase immunogenicity.

In contrast, proteins may have multiple domains that comprise a protein chain. Domains may be stable on their own or may require additional domains nearby (long range contacts). The individual protein chains containing the domains may be stable as a monomer or may require other protein chains nearby to be stable (long range contacts). As such, because of the large size of the IVB stem domain peptide, the protein is stable in vivo and as such no carrier is required.

As will also be apparent to one of skill in the art, these long-range contacts, that is, amino acids that are distant in sequence can be close in three-dimensional space if the peptide is folded properly. These structures are often important for the proper folding and stability of the peptide. Thus, the presence of these long-range contacts in an antigenic peptide are important for the preservation and presentation of as many native structures as possible to the host immune system.

In one embodiment of the invention, there is provided an IBV stem protein comprising the amino acid sequence as set forth in SEQ ID No:1.

(SEQ ID No: 1)
GFFGAIAGFLEGGWEGMIAGWHGYTSHGAHGVAVAADLKSTQEAINKIT

KNLNSLSELEVKNLQRLSGAMDELHNEILELDEKVDDLRADTISSQIEL

AVLLSNEGIINSEDEHLLALERKLKKMLGPSAVEIGNGCFETKHKCNQT

CLDRIAAGTFNAGEFSLPTFDSLNITAASLNDDGLDNHTILLYYSTAAS

SLAVTLMLAIFIVYMVSRDNVSCSICL.

In another embodiment of the invention, there is provided an IBV stem protein consisting of the amino acid sequence as set forth in SEQ ID No:1.

(SEQ ID No: 1)
GFFGAIAGFLEGGWEGMIAGWHGYTSHGAHGVAVAADLKSTQEAINKIT

KNLNSLSELEVKNLQRLSGAMDELHNEILELDEKVDDLRADTISSQIEL

AVLLSNEGIINSEDEHLLALERKLKKMLGPSAVEIGNGCFETKHKCNQT

CLDRIAAGTFNAGEFSLPTFDSLNITAASLNDDGLDNHTILLYYSTAAS

SLAVTLMLAIFIVYMVSRDNVSCSICL.

As will be apparent to one of skill in the art, it is possible that the combination of variations in sequence would have resulted in a mis-folded peptide that would have provided a strong immune response but little or no protection against IBV, as discussed herein. Furthermore, as discussed below, that is exactly what was seen when the vaccines of the invention were administered subcutaneously.

As discussed above, the consensus sequence as set forth in SEQ ID No:1 consists of amino acids that have the highest representation in all examined IBV HA2 sequences, for every position in the consensus.

There is also provided a consensus sequence of the IBV stem domain as set forth as SEQ ID No: 2.

(SEQ ID No: 2)
$G_1F_2F_3G_4A_5I_6A_7G_8F_9L_{10}E_{11}G_{12}G_{13}W_{14}E_{15}G_{16}M_{17}I_{18}A_{19}$ $G_{20}W_{21}H_{22}G_{23}Y_{24}T_{25}S_{26}H_{27}G_{28}A_{29}H_{30}G_{31}V_{32}A_{33}V_{34}A_{35}$ $A_{36}D_{37}L_{38}K_{39}S_{40}T_{41}Q_{42}E_{43}A_{44}I_{45}N_{46}K_{47}I_{48}T_{49}K_{50}N_{51}$ $L_{52}N_{53}S_{54}L_{55}S_{56}E_{57}L_{58}E_{59}V_{60}K_{61}N_{62}L_{63}Q_{64}R_{65}L_{66}S_{67}$ $G_{68}A_{69}M_{70}D_{71}E_{72}L_{73}H_{74}N_{75}E_{76}I_{77}L_{78}E_{79}L_{80}D_{81}E_{82}K_{83}$ $V_{84}D_{85}D_{86}L_{87}R_{88}A_{89}D_{90}T_{91}I_{92}S_{93}S_{94}Q_{95}I_{96}E_{97}L_{98}A_{99}$ $V_{100}L_{101}L_{102}S_{103}N_{104}E_{105}G_{106}I_{107}I_{108}N_{109}S_{110}E_{111}$ $D_{112}E_{113}H_{114}L_{115}L_{116}A_{117}L_{118}E_{119}R_{120}K_{121}L_{122}K_{123}$ $K_{124}M_{125}L_{126}G_{127}P_{128}S_{129}A_{130}V_{131}X_{132}I_{133}G_{134}N_{135}$ $G_{136}C_{137}F_{138}E_{139}T_{140}K_{141}H_{142}K_{143}C_{144}N_{145}Q_{146}T_{147}$ $C_{148}L_{149}D_{150}R_{151}I_{152}A_{153}A_{154}G_{155}T_{156}F_{157}X_{158}A_{159}$ $G_{160}E_{161}F_{162}S_{163}L_{164}P_{165}T_{166}F_{167}D_{168}S_{169}L_{170}N_{171}$ $I_{172}T_{173}A_{174}A_{175}S_{176}L_{177}N_{178}D_{179}D_{180}G_{181}L_{182}D_{183}$ $N_{184}H_{185}T_{186}I_{187}L_{188}L_{189}Y_{190}Y_{191}S_{192}T_{193}A_{194}A_{195}$ $S_{196}S_{197}L_{198}A_{199}V_{200}T_{201}L_{202}M_{203}X_{204}A_{205}I_{206}F_{207}$ $X_{208}V_{209}Y_{210}M_{211}X_{212}S_{213}R_{214}D_{215}N_{216}V_{217}S_{218}C_{219}$ $S_{220}I_{221}C_{222}L_{223}$.

wherein $X_{132}$ is D or E;
$X_{158}$ is N or D;
$X_{204}$ is I or L;
$X_{208}$ is I or V; and
$X_{212}$ is V or I.

In another embodiment of the invention, there is provided a IBV stem protein comprising the amino acid sequence as set forth in SEQ ID No: 2.

In another embodiment of the invention, there is provided a IBV stem protein consisting of the amino acid sequence as set forth in SEQ ID No: 2.

In yet other embodiments, there is provided an IBV stem protein comprising the amino acid sequence as set forth in SEQ ID No: 1 or SEQ ID No:2 with the proviso that the protein is flanked at either end thereof by at least two non-native amino acids.

As will be appreciated by one of skill in the art, "at least two non-native amino acids" refers to the two amino acids at the N-terminus and C-terminus respectfully, that is, immediately prior to $G_1$ and immediately after $L_{223}$ in the native Influenza Virus B Hemagglutinin sequence.

In yet other embodiments, there is provided an IBV stem protein consisting of the amino acid sequence as set forth in SEQ ID No: 1 or SEQ ID No:2 with the proviso that the protein is flanked at either end thereof by at least two non-native amino acids.

In some embodiments, the synthetic HA stem protein of the invention is linked to a peptide comprising an amino acid sequence corresponding to a secretion signal. Preferably, the peptide encoding the secretion signal is linked to the synthetic HA stem protein so that the signal sequence peptide is upstream of the synthetic HA stem protein. It is of note that the secretion signal is denoted as S in FIG. 3.

In some embodiments, the sequence of the signal sequence peptide is MLLAVLYCLLWSFQTSAGHFPRA (SEQ ID No:4) although other suitable signal sequences known in the art may be used within the invention.

In some embodiments, the HA stem protein of the invention is linked to a peptide encoding a trimerizing motif in order to facilitate formation of the trimerized protein. Preferably, the peptide encoding the trimerizing motif is linked to the HA stem peptide of the invention such that the trimerizing motif is downstream of the HA stem peptide. It is of note that the trimerizing motif is denoted as F in FIG. 3.

In some embodiments, the trimerization motif is YIPEAPRDGQAYVRKDGEWVLLSTFLG. (SEQ ID No:5)

In some embodiments of the invention, there is provided a polypeptide comprising in sequence a signal peptide and a protein comprising or consisting of the amino acid sequence as set forth in SEQ ID No:1 or SEQ ID No:2.

In some embodiments of the invention, there is provided a polypeptide comprising a protein comprising or consisting of the amino acid sequence as set forth in SEQ ID No:1 or SEQ ID No:2, and a trimerization peptide. In some embodiments, the trimerization peptide follows SEQ ID No:1 or SEQ ID No:2.

In some embodiments of the invention, there is provided a polypeptide comprising in sequence or in order a signal peptide, a protein comprising or consisting of the amino acid sequence as set forth in SEQ ID No:1 or SEQ ID No:2, and a trimerization peptide.

In some embodiments, the signal peptide comprises the amino acid sequence as set forth in SEQ ID No:4.

In some embodiments, the trimerization peptide comprises the amino acid sequence as set forth in SEQ ID No:5.

According to another aspect of the invention, there is provided a nucleic acid or a nucleic acid molecule or an oligonucleotide comprising the nucleotide sequence as set forth in SEQ ID NO: 3.

(SEQ ID No: 3)
GGGTTTTTCGGCGCCATCGCCGGCTTCCTGGAGGGCGGCTGGGAGGGCA

TGATCGCCGGCTGGCACGGCTACACCAGCCACGGCGCCCACGGCGTGGC

CGTGGCCGCCGACCTGAAGAGCACCCAGGAGGCCATTAACAAGATCACA

AAGAACCTGAACAGCCTGTCCGAGCTGGAGGTGAAGAACCTGCAGAGGC

TGAGTGGCGCCATGGATGAGCTGCACAACGAGATCCTGGAGCTGGACGA

GAAGGTGGATGACCTGAGGGCTGACACCATCAGCTCTCAGATTGAGCTG

GCCGTGCTGCTGTCTAACGAGGGCATCATCAACAGCGAGGACGAGCACC

TGCTGGCCCTGGAGAGAAAGCTGAAGAAGATGCTGGGACCCTCCGCCGT

GGAGATCGGAAACGGCTGCTTTGAGACCAAGCACAAGTGCAACCAGACC

TGTCTGGACAGAATCGCCGCCGGCACCTTCAATGCCGGAGAGTTCAGCC

TGCCCACCTTCGACAGCCTGAACATCACCGCCGCTAGCCTGAACGACGA

CGGACTGGACAACCACACCATCCTGCTGTACTACAGCACAGCCGCCAGC

TCCCTGGCCGTCACCCTGATGCTGGCCATCTTCATCGTGTACATGGTGA

GCAGAGATAACGTGTCTTGTTCCATCTGCCTG

According to a further aspect of the invention, there is provided a nucleic acid or nucleic acid molecule or oligonucleotide comprising a nucleic acid sequence deduced from the amino acid sequence of SEQ ID No: 1.

According to a further aspect of the invention, there is provided a nucleic acid or nucleic acid molecule or oligonucleotide comprising a nucleotide sequence deduced from the amino acid sequence of SEQ ID No: 2.

According to a further aspect of the invention, there is provided an expression system comprising the nucleic acid or nucleic acid molecule or oligonucleotide as set forth in SEQ ID No:3 or the nucleic acid or nucleic acid molecule or oligonucleotide deduced from the amino acid sequence of SEQ ID No:1 or the nucleic acid or nucleic acid molecule or oligonucleotide deduced from the amino acid sequence of SEQ ID No:2 operably linked to a suitable promoter.

In some embodiments, the nucleic acid may include a nucleic acid deduced from a signal peptide and/or a trimerization peptide as discussed above.

According to a further aspect of the invention, there is provided an expression system comprising the nucleic acid or nucleic acid molecule or oligonucleotide as set forth in SEQ ID No:3 operably linked to a suitable promoter.

According to a further aspect of the invention, there is provided an expression system comprising the nucleic acid or nucleic acid molecule or oligonucleotide deduced from the amino acid sequence of SEQ ID No:1 operably linked to a suitable promoter.

According to a further aspect of the invention, there is provided an expression system comprising the nucleic acid or nucleic acid molecule or oligonucleotide deduced from the amino acid sequence of SEQ ID No:2 operably linked to a suitable promoter.

In some embodiments, the expression system is a viral expression system for expression in mammalian cells, for example, in human cells.

According to another aspect of the invention, there is provided a method of immunizing an individual in need of such treatment against Influenza virus B comprising administering to said individual an effective amount of the protein as set forth in SEQ ID No:1 or SEQ ID No:2.

According to another aspect of the invention, there is provided a method of immunizing an individual in need of such treatment against Influenza virus B comprising administering to said individual an effective amount of the protein as set forth in SEQ ID No:2.

According to another aspect of the invention, there is provided a method of immunizing an individual in need of such treatment against Influenza virus B comprising administering to said individual an effective amount of the protein as set forth in SEQ ID No:1.

An "effective amount", as discussed herein, is an amount that is sufficient to generate an immune response against the antigen, that is, the protein as set forth in SEQ ID No:1 or SEQ ID No:2.

As used herein, "an individual in need of such treatment" refers to a person who is at significant risk of being infected by influenza virus B or who is at risk of suffering moderate to severe complications from influenza.

For example, moderate to severe complications include by are by no means limited to sinus and ear infections; inflammation of heart, brain or muscle tissue; pneumonia; and sepsis.

An "individual in need of such treatment" may be an individual who is at a higher risk of being exposed to influenza virus B than the general population, for example, a health care worker or individuals who encounter or interact with large groups of people on a daily basis.

An "individual in need of such treatment" may also be an individual who is at risk of suffering moderate to severe complications from influenza, for example, young children, adults aged 65 years or older, pregnant women, individuals with chronic lung disease, chronic heart disease or other chronic medical conditions, and individuals with asthma.

In some embodiments, the individual or person is a human.

According to another aspect of the invention, there is provided use of the protein as set forth in SEQ ID No:1 or SEQ ID No:2 for immunizing an individual against Influenza virus B.

According to another aspect of the invention, there is provided the protein as set forth in SEQ ID No:1 or SEQ ID No:2 for immunizing an individual in need of such treatment against Influenza virus B comprising administering to said individual an effective amount.

As will be apparent to one of skill in the art, an individual immunized or vaccinated against Influenza virus B as discussed above will be less likely to develop influenza because as a result of infection by Influenza virus B or to have an Influenza virus B infection establish than an individual of similar age and condition who has not been vaccinated. For example, such an individual may be 40% less likely, 50% less likely, 60% less likely or more than 70% less likely.

Specifically, most influenza vaccines known in the art reduce the risk of influenza in immunized individuals by 40-60%, provided that the influenza vaccine is effective against the circulating virus strains for that flu season.

However, the vaccine described herein has the significant advantage in that it is effective against all Influenza virus B strains, meaning that the vaccine will have the same effectiveness every year, regardless of what Influenza B strains are circulating in a given year.

An immunized individual who is infected with Influenza virus B may suffer less severe symptoms compared to an individual of similar age and condition who was not immunized. That is, influenza vaccination is known to make influenza milder if an immunized individual is infected with Influenza virus B.

For example, an immunized individual may suffer less severe or shorter duration of fever; feeling feverish; feeling chills; sore throat; runny or stuffy nose; headaches; and fatigue.

As will be appreciated by one of skill in the art, "an effective amount" of the protein as set forth in SEQ ID No:1 or SEQ ID No:2 can be administered by a variety of means. For example, isolated or purified protein, may be administered in combination with a suitable adjuvant and suitable immunological and/or pharmacological excipients as discussed herein. Such suitable adjuvants and excipients are known in the art and selection thereof is well within routine experimentation by one of skill in the art of vaccine preparation particularly in view of the examples provided herein.

For example, the vaccine may be formulated for intranasal administration or for subcutaneous administration. In some embodiments, the vaccine is formulated for intranasal administration.

Alternatively, the "effective amount" may be delivered by other means, for example, indirectly, by vaccination with an expression system. Specifically, as will be appreciated by one of skill in the art, in these embodiments, an expression system is administered to the individual and once the expression vector has been internalized by the cells of the individual, the peptide of the invention is synthesized within cells of the individual. As discussed above, the peptide may be linked to for example a signal sequence and/or a trimerization motif. However, the end result is that the peptide of the invention is administered to the individual, that is, the individual in need of such treatment.

For example, the expression system may be a viral vector or naked nucleic acid vector or a virus-like particle.

The viral expression vector may be selected from the group consisting of vaccinia vector, adenoviral vector, adeno-associated virus (AAV), cytomegalovirus vector, Sendai virus vectors and the like.

In some embodiments, the viral vector system is an adenoviral vector.

In some embodiments, the adenoviral vector is Ad5 or is derived therefrom.

As discussed above, in some embodiments, the expression system is an adenoviral expression system, for example, adenovirus serotype 5 or Ad5. Ad5 has attracted attention as a vector for gene therapy and vaccination due to its ability to efficiently infect human cells and replicate to high titres. It provides for single-round replication, making it safer than other replication-competent vectors. Furthermore, the adenoviral system is also known to be very effective in mucosal immunization.

As discussed below, murine experiments were done using an Ad5 vector as the delivery method. In some experiments, the construct included CD40L as an adjuvant. CD40L is a known molecular adjuvant; however, CD40L is not an antigen, and although it has been shown to stimulate the immune system and sustain immune response, the use of CD40L, or any adjuvant, is not essential to the use of the invention. The Ad5-vectored construct was shown in challenge studies to provide 100% protection. The challenge strain was selected based on infectivity and availability and is known to cause lethal infection in unvaccinated mice.

Specifically, there are two vaccine constructs: rAd-HBHA2F is the synthetic hemagglutinin protein (HA2 subunit of HA) without CD40 ligand while rAd-HBHA2FCD40L includes a CD40 ligand.

It is of note that in some embodiments, the protein is expressed as a recombinant protein in a mammalian, plant or microbial system (yeast or bacterial). In these embodiments, the purified recombinant HA stem protein could be administered as a vaccine and in these embodiments an adjuvant could be used such as aluminum salt, organic adjuvants such as squalene or oil based adjuvants, or Toll-like receptor ligands could be used in combination with the purified or isolated protein. Other suitable adjuvants known in the art may be used within these embodiments of the invention.

As discussed herein, in some experiments, the route of administration was subcutaneous and in others the route was intranasal. While both routes resulted in a robust antibody response, that is, generation of antibodies specific to the stem domain of HA, only the intranasal route provided protection. This suggests that protection is cell mediated and not humoral.

Specifically, while not wishing to be bound to a particular theory or hypothesis, the inventors believe that cellular immunity is much more important as very minimal neutralising activity of the serum was seen, suggesting that the antibodies induced by the vaccine have minimal neutralising activities. It is possible that the antibodies may be involved in ADCC (antibody-mediated cytotoxicity). However, there is very strong evidence that the vaccine induces cellular mediated immune responses as demonstrated by strong TNF-alpha, IL-2 and interferon gamma expression, as shown in Table 1.

Consequently, intranasal administration is preferable as it is effectively eliciting mucosal immunity which is better against respiratory virus infection (in this case influenza). Adenovirus (wild type) is naturally a respiratory virus so it can effectively replicate in the respiratory system (trachea or lungs). As such, the adenoviral vector is a very effective vector for mucosal delivery and consequently can induce robust immune response against influenza. Specifically, as discussed herein and as shown in Table 1, increased levels of IL-2, Interferon gamma and TNF-alpha were observed, suggesting that cell mediated immune responses may play a predominant role in protection. On the contrary, the antibodies obtained from circulating blood are ineffective in neutralising the virus.

Subcutaneous injection was tried but as discussed herein, it is far less effective.

At present, 100% of the vaccinated animals survived viral challenge whereas 50% of animals in the control group died. In addition to survival data, lung tissue samples were examined for pathological changes, which is independently another end point of protection. It was found the vaccinated groups show NO damage at all following virus challenge while significant pneumonia was observed in the lung tissues in the control group. This indicates very good protection of vaccinated individuals, as discussed herein.

The invention will now be described by way of examples; however, the invention is not necessarily limited by the examples.

The mice were immunised on day 0 with two different doses (10^8 or 10^9) by two different route (sub-cutaneous or intra-nasak routes of adimiristration). The animals were then boosted 28 days later (or w/o boost). Blood was drawn before challenging the mice with the IVB virus (day 56) for antibody titre analyses. The sera were then analysed in an ELISA assay where recombinant HA2 proteins were used to detect the antibodies. The results are shown in FIG. 4 where panels A and B shows that the vaccine with CD40 ligand after intra-nasal administration had antibodies titres that were higher than the vector controls. As can be seen, the controls are essentially flat. Panels C & D shows the same result except that the route is sub-cutaneous administration.

Figure 5:
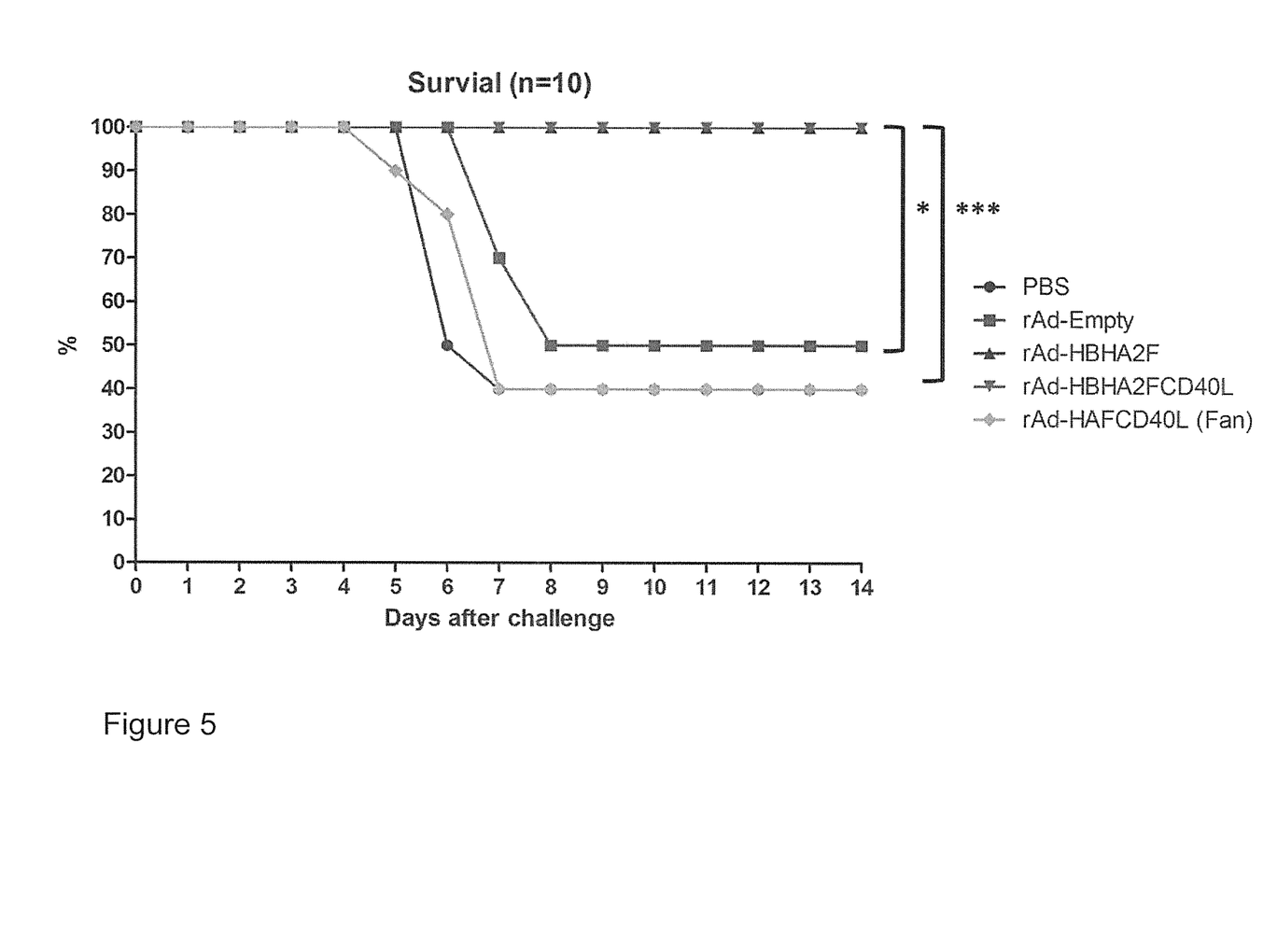
FIG. 5 shows survival results of vaccinated animals and controls post viral challenge.

Survival rates post challenge are shown in FIG. 5. As can be seen from the data, the vaccines with or without CDL afforded 100% protection whereas 50-60% of the test animal died following viral challenge on day 56. The data shown are from one experiment with n=10 mice per treatment group. *** $p<0.001$ one-way ANOVA with Bonferroni post test.

Virus titres in the lungs of the animals were measured following virus challenge, and it was found that the vaccine with or without CD40 Ligand had 2 logs lower virus detected in the lungs of the animals than the controls.

Figure 6A:
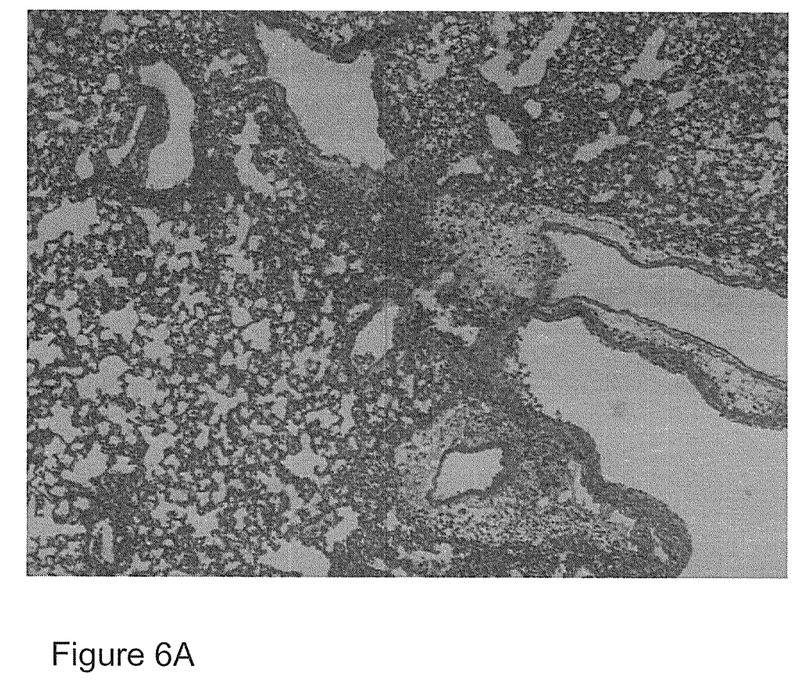
FIG. 6 shows pathological changes in lungs from animals post virus challenging. Panel A is a sample of lung tissue from an animal without vaccine (vector control). Panel B is a sample of lung tissue from the vaccinated group.
Figure 6B:
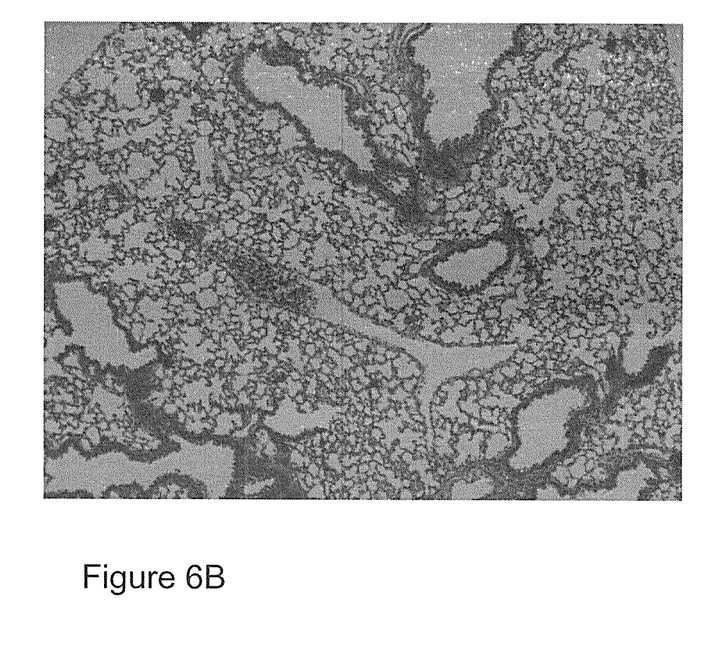

As shown in FIG. 6, lung tissue from animals was examined to see what pathological changes, if any, occurred post viral challenge. As shown in panel A, the pathological signs of severe pneumonia as demonstrated by massive infiltration of mononuclear cells and inflammatory damages in the tissues can be seen in the vector control group. In contrast, in panel B, which is lung tissue from the vaccinated group, the lung tissue sample shows no tissue damage at all.

The scope of the claims should not be limited by the preferred embodiments set forth in the examples but should be given the broadest interpretation consistent with the description as a whole.

REFERENCES

1. Carrat, F. and Flahault, A. Influenza vaccine: the challenge of antigenic drift. *Vaccine*. 25, 6852-62 (2007)
2. Caini S, Huang Q S, Ciblak M A, et al. Epidemiological and virological characteristics of influenza B: results of the global influenza B study. Influenza Other Respir Viruses. 2015; 9:3-12.
3. Hashem A, C Gravel, Z Chen, Y Yi, M Tocchi, B Jaentschke, X Fan, C Li, M Rosu-Myles, A Pereboev, R He, J Wang, X Li. CD40L preferentially modulates immune response and enhances protection against influenza virus. *J. Immunol.* 2014 Jul. 15; 193(2):722-34. doi: 10.4049/jimmunol.1300093

TABLE 1

| | Cytokine levels | | | |
|---|---|---|---|---|
| | IL-2 | γ-Interferon | TNF-α | GM-CSF |
| PBS Control | 2.5 | N.D. | N.D. | N.D. |
| Vector Control | 2.0 | N.D | N.D. | N.D. |
| rAd-HBHA2F | 4.8 | 10 | 2 | 2 |
| rAd-HBHA2F CD40L | 8.0 | 300 | 7 | 25 |

N.D.—none detectable

---

The invention claimed is:

1. A synthetic IBV HA2 stem protein consisting of the amino acid sequence as set forth in SEQ ID No:2.

2. The synthetic IBV HA2 stem protein according to claim 1 wherein the synthetic IBV HA2 stem protein is linked to a peptide comprising an amino acid sequence corresponding to a secretion signal.

3. The synthetic IBV HA2 stem protein according to claim 2 wherein the peptide encoding the secretion signal is linked to the IBV HA2 stem protein so that the signal sequence peptide is upstream of the IBV HA2 stem protein.

4. A nucleic acid molecule comprising a synthetic IBV HA2 stem protein consisting of the nucleic acid molecule deduced from the amino acid sequence of SEQ ID No:2 operably linked to a suitable expression system promoter.

5. A viral expression system comprising: a synthetic IBV HA2 stem protein consisting of the nucleic acid molecule as set forth in SEQ ID No:3; or consisting of the nucleic acid molecule deduced from the amino acid sequence of SEQ ID No:1; or consisting of the nucleic acid molecule deduced from the amino acid sequence of SEQ ID No:2; said nucleic acid molecule operably linked to a suitable expression system promoter, wherein the viral expression system is an adenoviral vector.

6. The viral expression system according to claim 5 wherein the adenoviral vector is Ad5.

7. A method of immunizing an individual in need of such treatment against Influenza virus B comprising administering to said individual an effective amount of an IBV HA2 stem protein consisting of the amino acid sequence as set forth in SEQ ID No:1 or SEQ ID No:2.

8. The method according to claim 7 wherein the individual in need of such treatment is a person who is at significant risk of being infected by influenza virus B.

9. The method according to claim 7 wherein the individual who is in need of such treatment is an individual who is at risk of suffering moderate to severe complications from influenza.

10. The method according to claim 7 wherein the individual in need of such treatment is an individual who is at a higher risk of being exposed to influenza virus B than the general population.

11. The method according to claim 7 wherein the individual is a young child, an adult aged 65 years or older, a pregnant woman, an individual with asthma or an individual with chronic lung disease, chronic heart disease or another chronic medical condition.

12. The method according to claim 7 wherein the IBV HA2 stem protein is administered intranasally.

13. The method according to claim 7 wherein the IBV stem protein is arranged to be expressed by an expression system.

14. The method according to claim 13 wherein the expression system is a viral expression vector or a naked nucleic acid vector or a virus-like particle.

15. The method according to claim 14 viral expression vector is selected from the group consisting of vaccinia vector, adenoviral vector, adeno-associated virus (AAV), cytomegalovirus vector, and sendai virus vector.

16. The method according to claim 15 wherein the viral vector system is an adenoviral vector.

17. The method according to claim 7 wherein the IBV HA2 stem protein is linked to a peptide comprising an amino acid sequence corresponding to a secretion signal.

18. The method according to claim 17 wherein the peptide encoding the secretion signal is linked to the IBV HA2 stem protein so that the signal sequence peptide is upstream of the IBV HA2 stem protein.

19. The method according to claim 7 wherein the IBV HA2 stem protein is linked to a peptide encoding a trimerizing motif.

20. The method according to claim 19 wherein the peptide encoding the trimerizing motif is linked to the IBV HA2 stem peptide such that the trimerizing motif is downstream of the IBV HA2 stem peptide.

21. The method according to claim 7 wherein the IBV step protein is expressed as a polypeptide comprising in order a signal peptide, the IBV HA2 stem protein consisting of the amino acid sequence as set forth in SEQ ID No:1 or SEQ ID No:2, and a trimerization peptide.

22. A method of immunizing an individual in need of such treatment against Influenza virus B comprising administering intranasally to said individual an effective amount of an IBV HA2 stem protein consisting of the amino acid sequence as set forth in SEQ ID No:1 or SEQ ID No:2, thereby inducing a cellular-mediated immune response in said individual.

23. The method according to claim 7 wherein the administration of the effective amount of the IBV HA2 stem protein induces a cellular-mediated immune response in said individual.

* * * * *